(12) United States Patent
Chen et al.

(10) Patent No.: US 9,506,864 B2
(45) Date of Patent: Nov. 29, 2016

(54) METHOD FOR PREPARING GOLD NANOCLUSTER COMPOSITION

(71) Applicant: Industrial Technology Research Institute, Hsinchu (TW)

(72) Inventors: Cheng-Tai Chen, Zhongli (TW); Pei-Shin Jiang, Hsinchu (TW); Ting-Shou Chen, Yangmei (TW); Jane S-C Tsai, Taipei (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 0 days.

(21) Appl. No.: 14/582,428

(22) Filed: Dec. 24, 2014

(65) Prior Publication Data

US 2016/0131582 A1    May 12, 2016

(30) Foreign Application Priority Data

Nov. 6, 2014   (TW) .............................. 103138484 A

(51) Int. Cl.
*G01N 21/64* (2006.01)
*G01N 21/00* (2006.01)
*C09K 11/06* (2006.01)
*C09K 11/00* (2006.01)

(52) U.S. Cl.
CPC ........... *G01N 21/6428* (2013.01); *C09K 11/00* (2013.01); *C09K 11/06* (2013.01); *G01N 2021/6439* (2013.01)

(58) Field of Classification Search
CPC ..................... G01N 21/6447; G01N 21/6445; G01N 21/64; G01N 21/63; G01N 21/62; G01N 21/00; C09K 11/06; C09K 11/00
USPC ................. 436/80, 73, 120, 119; 252/301.16
See application file for complete search history.

(56) References Cited

U.S. PATENT DOCUMENTS

| | | | |
|---|---|---|---|
| 5,728,590 A | 3/1998 | Powell | |
| 7,413,770 B2 | 8/2008 | Huang et al. | |
| 7,914,588 B2 | 3/2011 | Martinez et al. | |
| 8,071,181 B2 | 12/2011 | Hegmann et al. | |
| 8,263,668 B2 | 9/2012 | Chang et al. | |
| 8,294,838 B2 | 10/2012 | Hegmann et al. | |
| 8,383,919 B2 | 2/2013 | Gao | |
| 8,734,844 B2 | 5/2014 | Lee et al. | |
| 2006/0154234 A1 | 7/2006 | Winther et al. | |
| 2007/0037138 A1 | 2/2007 | Winther | |
| 2007/0269594 A1 | 11/2007 | Ackerson et al. | |
| 2007/0269880 A1 | 11/2007 | Paknikar | |
| 2009/0212260 A1 | 8/2009 | Paknikar | |
| 2009/0298115 A1 | 12/2009 | Chang et al. | |
| 2010/0009427 A1 | 1/2010 | Martinez et al. | |
| 2011/0165689 A1 | 7/2011 | Ying et al. | |
| 2011/0300532 A1 | 12/2011 | Jahnen-Dechent et al. | |
| 2012/0100075 A1 | 4/2012 | Chang et al. | |
| 2012/0195833 A1 | 8/2012 | Lin et al. | |
| 2012/0267573 A1 | 10/2012 | Wu et al. | |
| 2013/0020503 A1* | 1/2013 | Geddes .............. G01N 21/6408 250/459.1 |
| 2013/0023714 A1 | 1/2013 | Johnston et al. | |
| 2013/0115710 A1* | 5/2013 | Geddes ................ C09K 11/025 436/172 |
| 2013/0130392 A1 | 5/2013 | Thalappil et al. | |
| 2013/0156938 A1* | 6/2013 | Geddes .................. G01N 21/64 427/8 |
| 2014/0179941 A1 | 6/2014 | Bao | |

FOREIGN PATENT DOCUMENTS

| | | |
|---|---|---|
| CN | 103115905 A | 5/2013 |
| GB | 365760 A | 1/1932 |
| TW | I318173 B | 12/2009 |
| WO | WO 02/077647 A1 | 10/2002 |
| WO | WO 2008/053484 A2 | 5/2008 |
| WO | WO 2012/104831 A1 | 8/2012 |

OTHER PUBLICATIONS

Chen et al., "Cysteine-directed fluorescent gold nanoclusters for the sensing of pyrophosphate and alkaline phosphatase," Journal of Materials Chemistry C, vol. 2, Apr. 1, 2014, pp. 4080-4085.
Dai et al., "Label-free turn-on fluorescent detection of melamine based on the anti-quenching ability of Hg2+ to gold nanoclusters," Biosensors and Bioelectronics, vol. 53, 2014 (available online Sep. 29, 2013), pp. 76-81.
Ding et al., "Dithiothreitol-capped fluorescent gold nanoclusters: An efficient probe for detection of copper(II) ions in aqueous solution," Biosensors and Bioelectronics, vol. 59, 2014 (available online Mar. 31, 2014), pp. 216-220.
Ding et al., "Templated in-situ synthesis of gold nanoclusters conjugated to drug target bacterial enoyl-ACP reductase, and their application to the detection of mercury ions using a test stripe," Microchimica Acta, 2014 (published online Feb. 23, 2014), pp. 1-6.
Joseph et al., "Synthesis of highly fluorescent gold nanoclusters using egg white proteins," Colloids and Surfaces B: Biointerfaces, vol. 115, 2014 (available online Nov. 20, 2013), pp. 46-50.
Li et al., "Sensitive iodate sensor based on fluorescence quenching of gold nanocluster," Analytica Chimica Acta, vol. 827, 2014 (available online Apr. 12, 2014), pp. 80-85.
Santhosh et al., "Selective and sensitive detection of free bilirubin in blood serum using human serum albumin stabilized gold nanoclusters as fluorometric and colorimetric probe," Biosensors and Bioelectronics, vol. 59, 2014 (available online Apr. 8, 2014), pp. 370-376.
Tao et al., "Engineered CpG-Antigen Conjugates Protected Gold Nanoclusters as Smart Self-Vaccines for Enhanced Immune Response and Cell Imaging," Advanced Functional Materials, vol. 24, 2014, pp. 1004-1010.

(Continued)

*Primary Examiner* — Christine T Mui
(74) *Attorney, Agent, or Firm* — Birch, Stewart, Kolasch & Birch, LLP

(57) ABSTRACT

A gold nanocluster composition and method for preparing the same are provided. The method includes providing a gold ion-containing solution. Next, the method entails mixing the gold ion-containing solution and a reducing agent solution to obtain a first mixture liquid, and heating the first mixture liquid to obtain a second mixture liquid, wherein the second mixture liquid contains the gold nanoclusters, which are partially capped by reducing agent.

5 Claims, 23 Drawing Sheets

(56) References Cited

OTHER PUBLICATIONS

Venkatesh et al., "Purine-Stabliz edGieen Fluorescent Gold Nanoclusters for Cell Nuclei Imaging Applications," Applied Materials & Interfaces, vol. 6, Jan. 20, 2014, pp. 2185-2191.

Xu et al., "Selectively fluorescent sensing of Cu2+ based on lysine-functionalized gold nanoclusters," Colloids and Surfaces A: Physicochemical and Engineering Aspects, vol. 450, 2014 (available online Mar. 15, 2014), pp. 115-120.

Yang et al., "Novel and remarkable enhanced-fluorescence system based on gold nanoclusters for detection of tetracycline," Talanta, vol. 122, 2014 (available online Dec. 10, 2013), pp. 36-42.

Zhuang et al., "Targeted surface-functionalized gold nanoclusters for mitochondrial imaging," Biosensors and Bioelectronics, vol. 55, 2014 (available online Dec. 10, 2013), pp. 76-82.

Chen et al., "Glutathione-bound gold nanoclusters for selective-binding and detection of glutathione S-transferase-fusion proteins from cell lysates," Chemical Communications, 2009 (First published as an Advance Article on the web Nov. 3, 2009), pp. 7515-7517 and pp. 1-9.

Taiwanese Office Action and Search Report for Taiwanese Application No. 103138484, dated Oct. 14, 2015.

Xu et al., "Study on Interaction Between Gold Nanoparticles and Glutathione and Its Analytical Application," Journal of Hebei University (Natural Science Edition), vol. 27, No. 3, May 2007, pp. 265-269, with an English abstract.

* cited by examiner

◯ : gold nanocluster 20

▯ : reducing agent 21

△ : thiol group 22

US 9,506,864 B2

METHOD FOR PREPARING GOLD NANOCLUSTER COMPOSITION

CROSS REFERENCE TO RELATED APPLICATIONS

The present application is based on, and claims priority from, Taiwan Application Serial Number 103138484, filed on Nov. 6, 2014, the disclosure of which is hereby incorporated by reference herein in its entirety

TECHNICAL FIELD

The technical field relates to a gold nanocluster composition and a method for preparing the same, and in particular it relates to a method utilizing a gold nanocluster composition for detecting a thiol-containing compound.

BACKGROUND

Recent research shows that when the size of the gold nanoparticles is reduced to that of the gold nanoclusters, they have specific fluorescent properties other than surface plasmon resonance. Because the gold nanoclusters have advantages such as a lower toxicity than the semiconductor fluorescence quantum dots and high light stability, the gold nanoclusters have great potential in the applications of biosensing and bioluminescence labeling. However, conventional methods for synthesizing the gold nanoclusters and modifying their surface are complicated and time-consuming. If bio-molecules should be conjugated on the gold nanoclusters, the more complicated and time-consuming processes cannot be omitted.

Accordingly, a process for easy preparation and surface modification of the gold nanoclusters is desired in the industry. Furthermore, the gold nanoclusters may utilize for detecting thiol-containing compounds.

SUMMARY

One embodiment of the disclosure provides a gold nanocluster composition, comprising: a gold nanocluster partially capped by reducing agent, and the gold nanocluster composition has fluorescence emission peaks at wavelength of 600-650 nm and 800-850 nm.

One embodiment of the disclosure provides a gold nanocluster composition, comprising: a gold nanocluster partially capped by reducing agent, and the gold nanocluster composition has a single fluorescence emission peak at wavelength of 800-900 nm.

One embodiment of the disclosure provides a method for preparing a gold nanocluster composition, comprising: mixing a gold ion-containing solution and a reducing agent solution to obtain a first mixture liquid; and heating the first mixture liquid to obtain a second mixture liquid, wherein the second mixture liquid contains a gold nanocluster composition, and the gold nanoclusters are partially capped by reducing agent.

One embodiment of the disclosure provides a method for detecting a thiol-containing compound, including: providing the described gold nanocluster compositions; providing an analyte to react with the gold nanocluster compositions; and analyzing the reaction result to check whether the analyte contains a thiol-containing compound or not.

A detailed description is given in the following embodiments with reference to the accompanying drawings.

BRIEF DESCRIPTION OF THE DRAWINGS

The disclosure can be more fully understood by reading the subsequent detailed description and examples with references made to the accompanying drawings, wherein.

DETAILED DESCRIPTION

Figure 1:
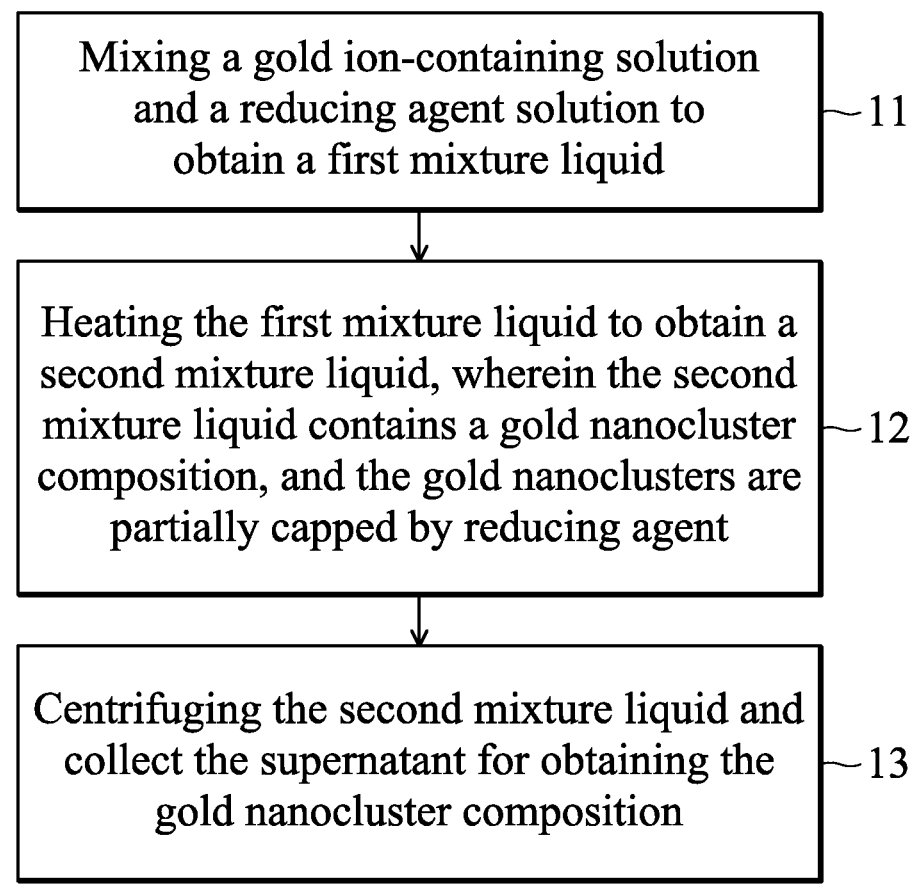
FIG. 1 shows a flow chart of preparing a gold nanocluster composition in one embodiment of the disclosure.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

FIG. 1 shows a flow chart of preparing a gold nanocluster composition in one embodiment of the disclosure. First, a gold ion-containing solution and a reducing agent solution are mixed to form a first mixture liquid in step 11. In one embodiment, the gold ion-containing solution can be chloroauric acid solution, auric chloride solution, gold sulfide solution, or a combination thereof. The reducing agent can be glutathione (GSH). When the gold ions and the reducing agent have a molar ratio of 1:0.9 to 1:1.4, a gold nanocluster composition formed from that may simultaneously have dual fluorescence emission peaks, e.g. at wavelength of 600-650 nm and 800-850 nm. When the gold ions and the reducing agent have a molar ratio of 1:0 to 1:0.6, a mixing liquid formed from that has no fluorescence. When the gold ions and the reducing agent have a molar ratio of 1:1.5 to 1:2, a gold nanocluster composition formed from that has deformed fluorescence emission peaks. The fluorescence emission at wavelength of 700 nm of a gold nanocluster composition will be weakened by increasing the molar ratio of the reducing agent.

Subsequently, the first mixture liquid is heated to form a second mixture liquid in step 12. In one embodiment, the heating step can be performed by a general heating method such as with a dry bath heater or a microwave heater. In one embodiment, the heating step is performed by microwave power of 270 W to 450 W for a period of 10 minutes to 60 minutes. The gold ions cannot completely react to form a gold nanocluster composition by overly low microwave power or an overly short heating period. The gold ions easily form larger gold nanoparticles by overly high microwave power or an overly long heating period. The second mixture liquid formed by the heating process contains the gold nanocluster compositions, wherein the gold nanoclusters are partially capped by reducing agent. The term "partially" means that not the entire surface of each of the gold nanoclusters is fully capped by reducing agent, and some unoccupied sites on the surface of the gold nanoclusters remain.

Finally, the second mixture liquid can be centrifuged in step 13 to collect the supernatant for obtaining the gold nanocluster compositions. The solution containing gold nanocluster compositions is stored at 4° C. for further use. In some embodiments, the rotation speed of the centrifugal step is 10000 rpm to 14000 rpm. In another embodiment, the factors of the centrifugal step such as rotation speed, rotation period, and rotation frequency are not limited. Only if the gold nanocluster compositions can be separated by a set of centrifugal factors, the set of factors are accepted.

In another embodiment, the steps 11 to 13 are repeated, the difference being that the gold ions and the reducing agent have a molar ratio of 1:0.7 to 1:0.8, and the other process factors of the heating step and the centrifugal step are similar to the above embodiment. As such, the gold nanoclusters are partially capped by reducing agent, and the gold nanocluster compositions have a single fluorescence emission peak at wavelength of 800 nm to 900 nm.

The fluorescent gold nanocluster compositions may serve as signal molecules due to their specific optical properties. The gold nanocluster compositions allow for easy modification for different applications, such as biomedicine (e.g. detection, imaging, and drug release therapy). The gold nanocluster compositions with the specific emission properties can be applied as a novel optoelectronic material or sensor for environmental safety, food safety, and elsewhere in the food industry.

One embodiment of the disclosure provides a method of detecting a thiol-containing compound, including: providing the gold nanocluster compositions to be reacted with an analyte, and analyzing the reaction result to check whether the analyte contains a thiol-containing compound or not. In one embodiment, the analyte is in liquid form or gas form. The mixture of the gold nanocluster compositions and the analyte can be immediately characterized by a fluorescence spectroscopy analysis system for measuring the emission intensity at a specific wavelength. For example, the specific wavelength is 600-650 nm and 800-850 nm. While the analyte contains a thiol-containing compound, the fluorescence emission intensity at wavelength of 600-650 nm increases, and the fluorescence emission intensity at wavelength of 800-850 nm decreases.

Below, exemplary embodiments will be described in detail with reference to accompanying drawings so as to be easily realized by a person having ordinary knowledge in the art. The inventive concept may be embodied in various forms without being limited to the exemplary embodiments set forth herein. Descriptions of well-known parts are omitted for clarity, and like reference numerals refer to like elements throughout.

EXAMPLES

Preparation of the Gold Nanocluster Compositions

Example 1

Figure 2:
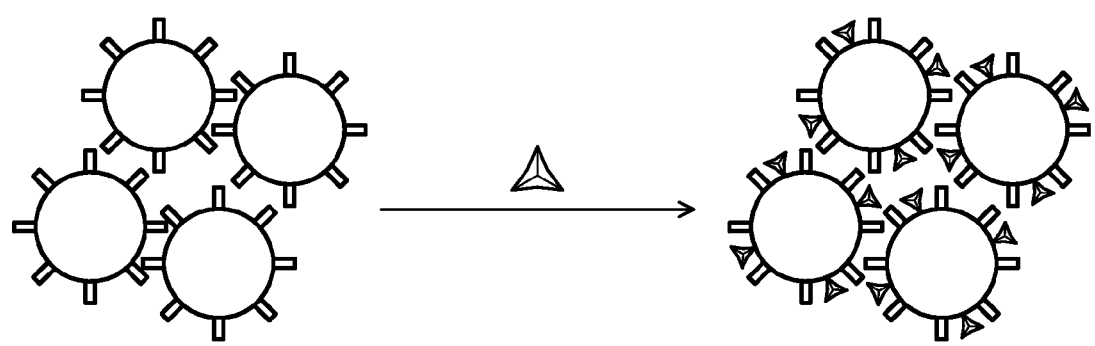
FIG. 2 shows the gold nanocluster compositions are partially capped by glutathione in one embodiment of the disclosure.

5 mM chloroauric acid ($HAuCl_4$) solution and 5 mM glutathione (L-glutathione, GSH) solution were prepared. 0.2 mL of $HAuCl_4$ solution and 0.2 mL of GSH solution were added to a microcentrifuge tube, wherein the molar ratio of $HAuCl_4$ and GSH was 1:1. The tube was then completely shaken for 5 minutes using a vortex mixer to obtain a first mixture liquid. The microcentrifuge tube was opened and then put into a domestic microwave oven, heated by microwave power of 270 W for 30 minutes, and then heated by microwave power of 450 W for 30 minutes to obtain a second mixture liquid. The microcentrifuge tube was cooled to room temperature and then centrifuged at 12000 rpm for 10 minutes. The supernatant was collected to obtain a liquid containing the gold nanocluster compositions. Concentrations of $HAuCl_4$ solution and GSH solution could be controlled to tune the fluorescence emission peak range of the gold nanocluster compositions. As shown in FIG. 2, the gold nanoclusters (20) are partially capped by GSH (21).

Example 2

5 mM $HAuCl_4$ solution and 5 mM GSH solution were prepared. 0.2 mL of $HAuCl_4$ solution and 0.2 mL of GSH solution were added to a glass sample vial, wherein the molar ratio of $HAuCl_4$ and GSH was 1:1. The tube was then completely shaken for 10 seconds using a vortex mixer to obtain a first mixture liquid. The glass sample via was opened and then put into a dry bath heater, heated from room temperature to 120° C. for 10 minutes, and then heated at 120° C. for 50 minutes to obtain a second mixture liquid. The glass sample vial was cooled to room temperature and then the solution was centrifuged at 12000 rpm for 10 minutes. The supernatant was collected to obtain a liquid containing the gold nanocluster compositions.

Example 3

Figure 3A:
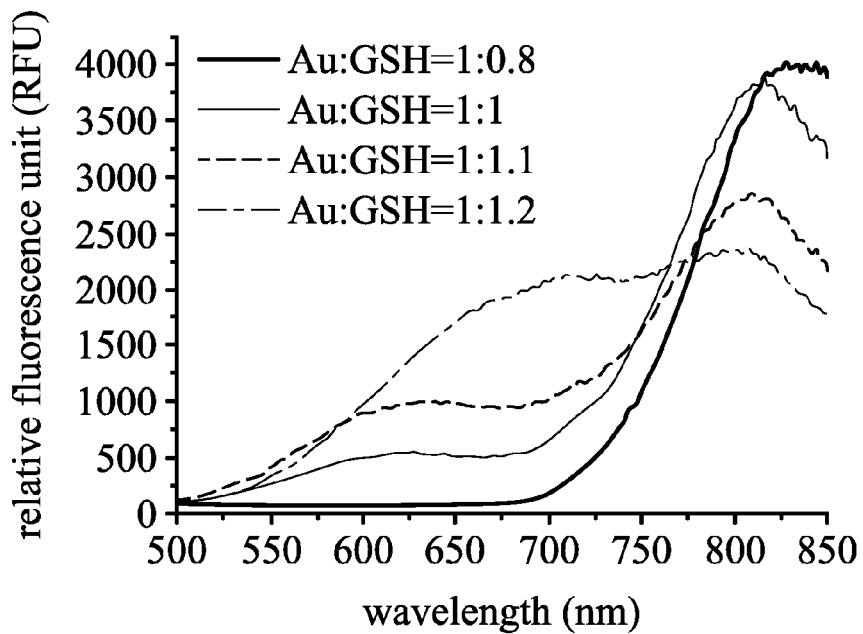
FIGS. 3A-3B, 4, 5, and 6 show the specific fluorescence spectra of the gold nanocluster compositions prepared at different molar ratios of gold ions to glutathione in embodiments of the disclosure.
Figure 3B:
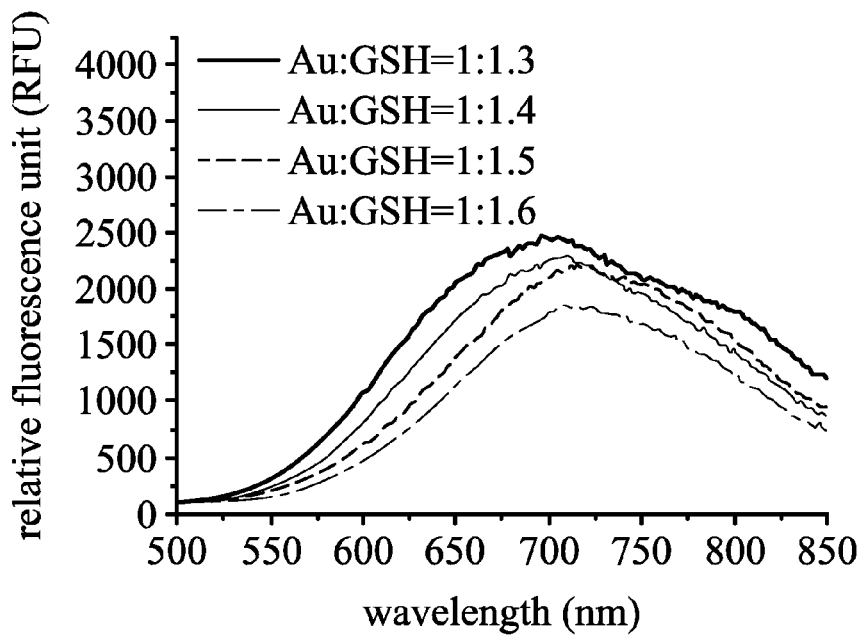

Example 3 was similar to Example 1, and the difference in Example 3 was the concentration of GSH solution being changed to achieve different molar ratios of $HAuCl_4$ and GSH, such as Au:GSH=1:1.1, 1:1.2, 1:1.3, 1:1.4, 1:1.5, and 1:1.6. When the Au:GSH was 1:1.1, the gold nanocluster compositions still had dual fluorescence emission peaks. When the Au:GSH was 1:1.2, the fluorescence emission peaks of the gold nanocluster compositions began to deform as shown in FIGS. 3A-3B.

Example 4

Figure 4:
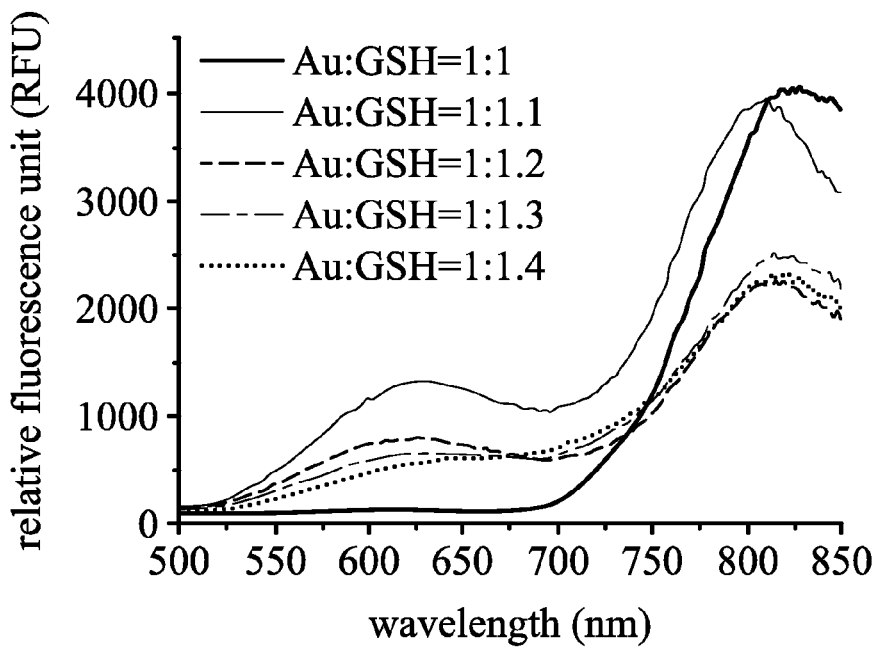

Example 4 was similar to Example 2, and the difference in Example 4 was the concentration of GSH solution being changed to achieve different molar ratios of $HAuCl_4$ and GSH, such as Au:GSH=1:1.1, 1:1.2, 1:1.3, and 1:1.4. The gold nanocluster compositions had dual fluorescence emission peaks, as shown in FIG. 4.

Example 5

Example 5 was similar to Example 1, and the difference in Example 5 was the concentration of GSH solution being changed to achieve a different molar ratio of $HAuCl_4$ and GSH, such as Au:GSH=1:0.8. The fluorescence emission spectrum of the gold nanocluster compositions is shown in FIG. 3A. Note that the gold nanocluster compositions prepared by above Au:GSH molar ratio only has a single fluorescence peak at the near-infrared region with a wavelength greater than 800 nm, other than dual fluorescence emission peaks at wavelength of 600-650 nm and 800-850 nm.

Comparative Example 1

Figure 5:
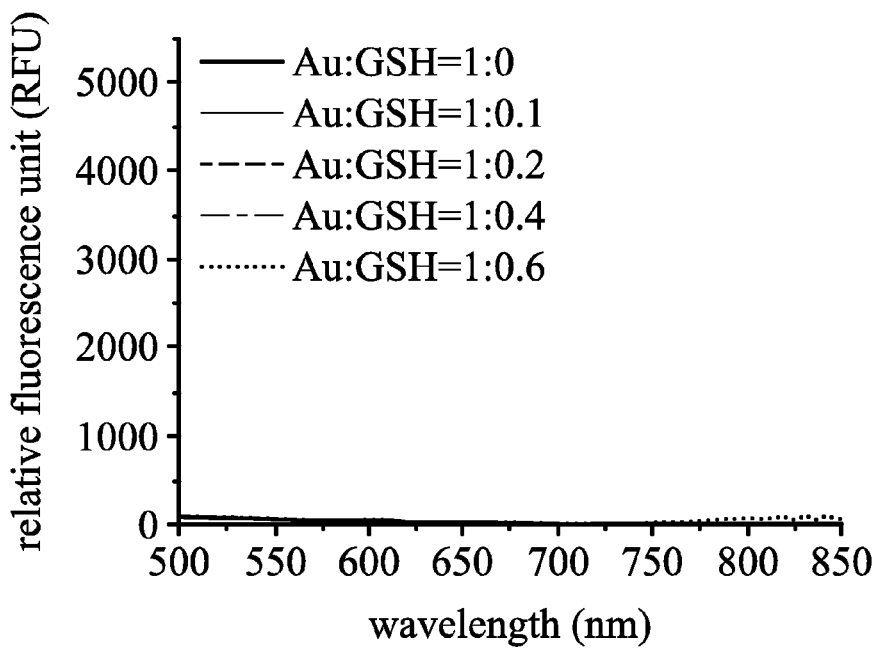

Comparative Example 1 was similar to Example 1, and the difference in Comparative Example 1 was the concentration of GSH solution being changed to achieve different molar ratios of $HAuCl_4$ and GSH, such as Au:GSH=1:0, 1:0.1, 1:0.2, 1:0.4, and 1:0.6. The products prepared from the above Au:GSH molar ratios had no fluorescent properties, as shown in FIG. 5.

Comparative Example 2

Figure 6:
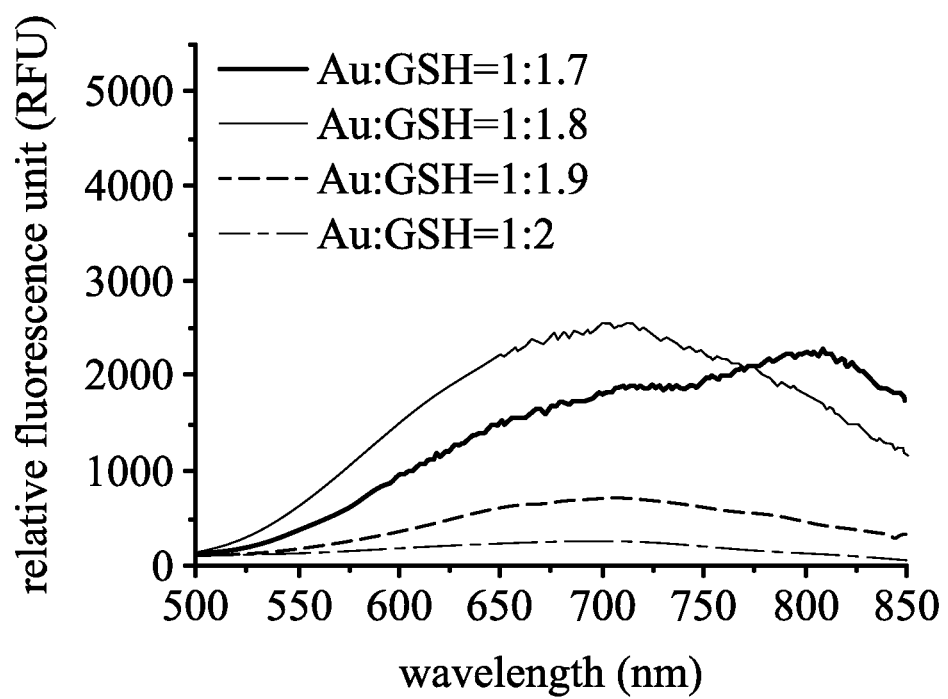
Figure 7A:
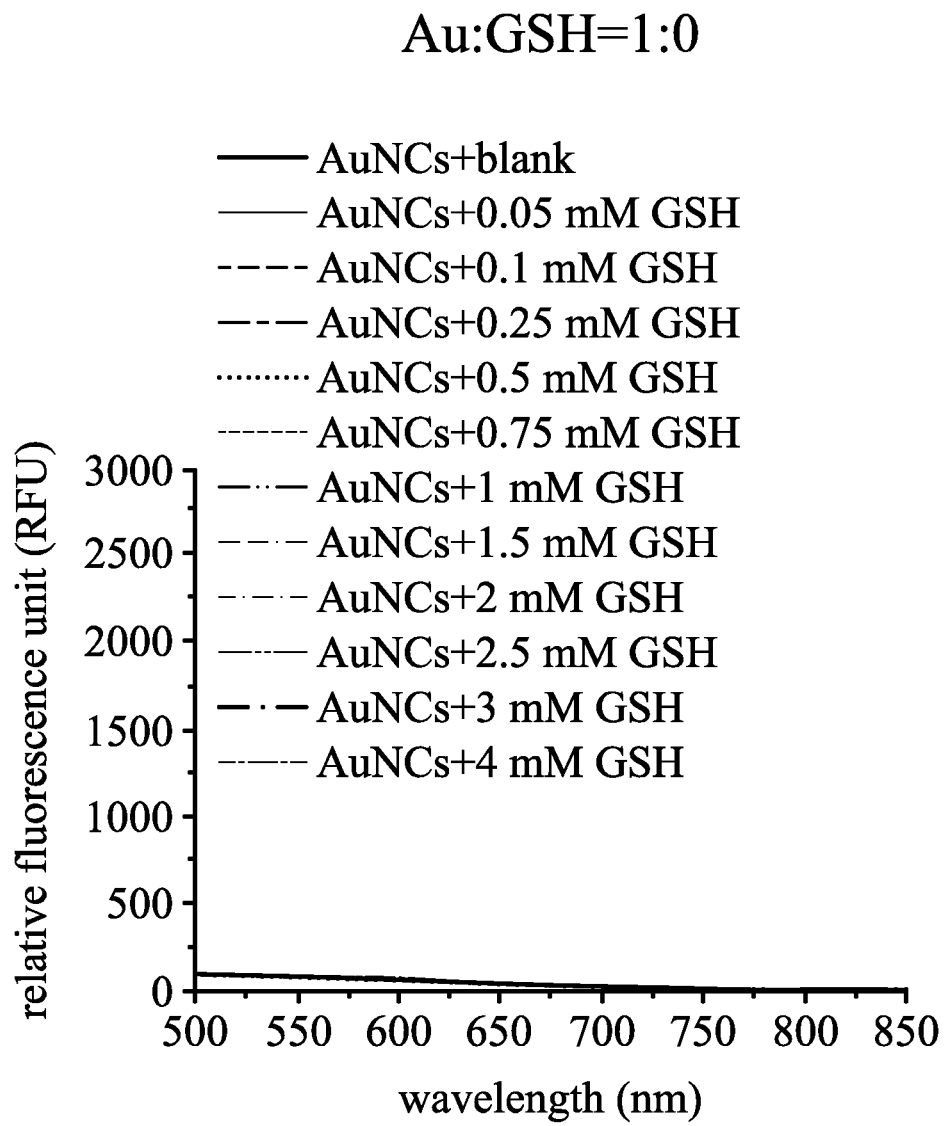
FIGS. 7A-7E and 8A-8E show the fluorescence spectra of the gold nanocluster compositions (prepared at different molar ratios of gold ions to glutathione) detecting thiol-containing compounds from liquid analytes in embodiments of the disclosure.
Figure 7B:
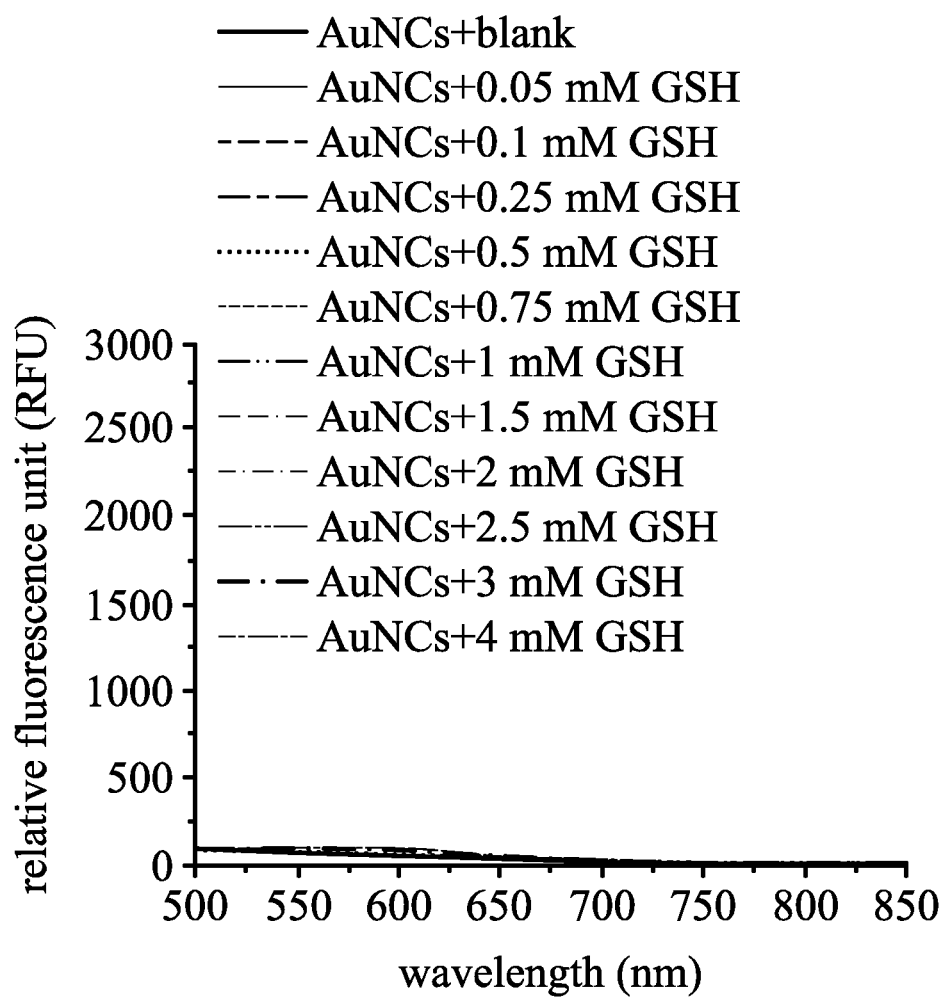
Figure 7C:
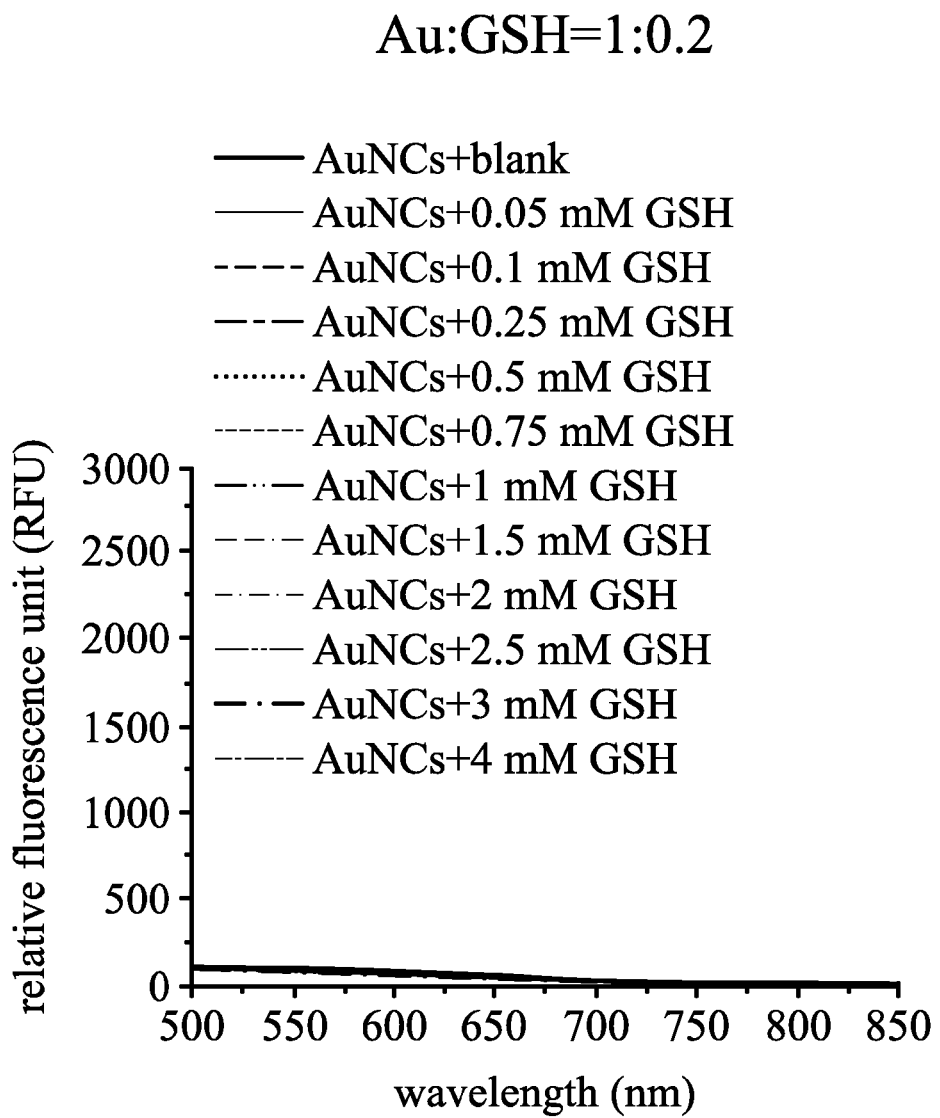
Figure 7D:
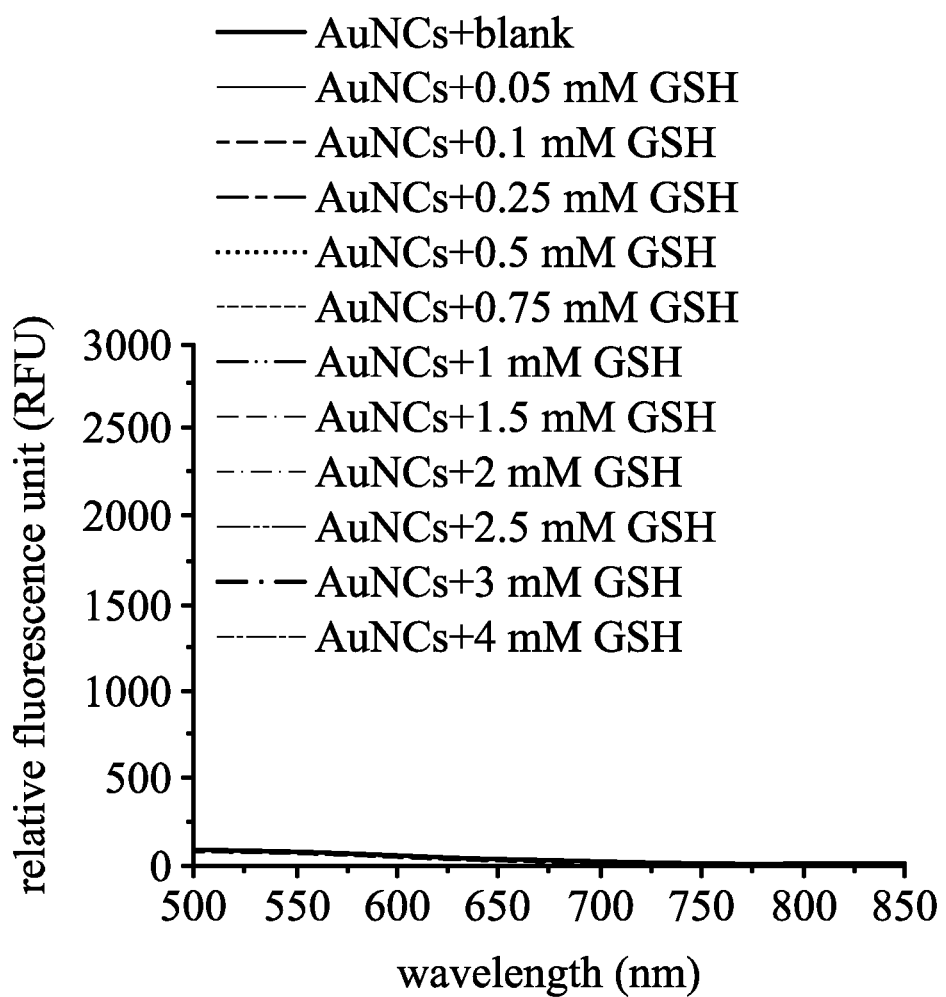
Figure 7E:
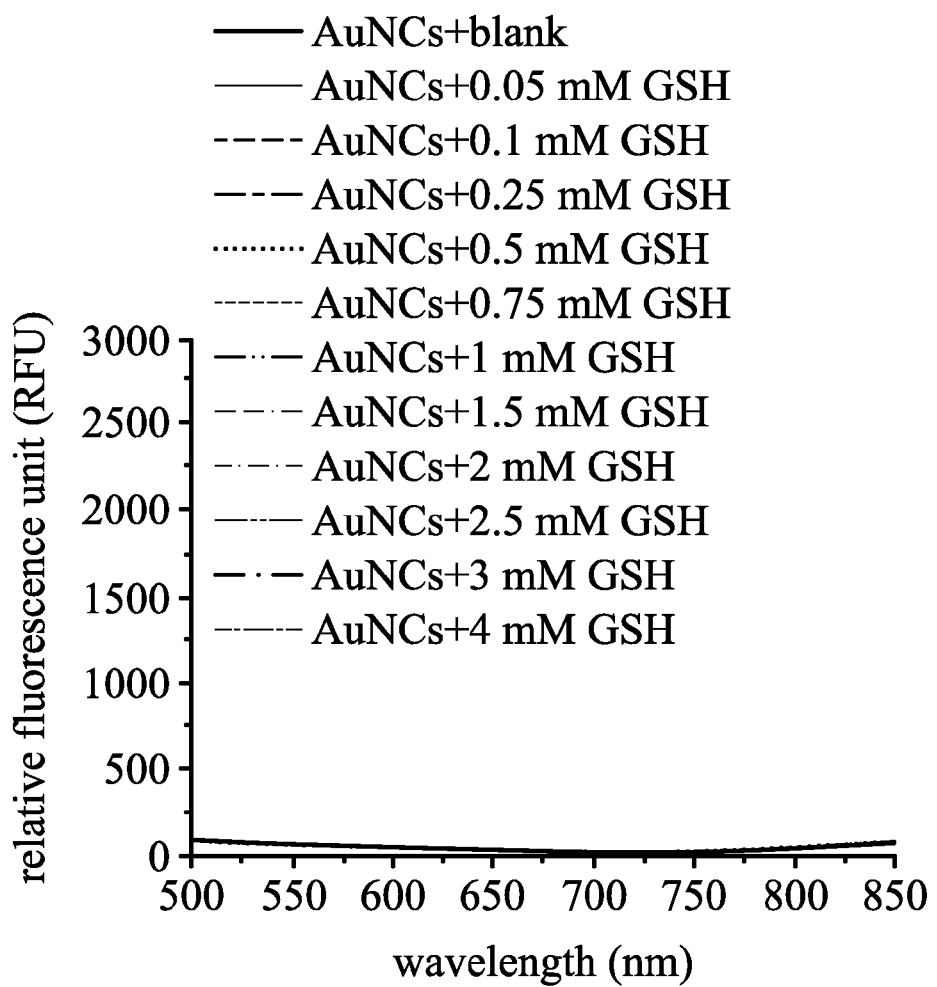
Figure 8A:
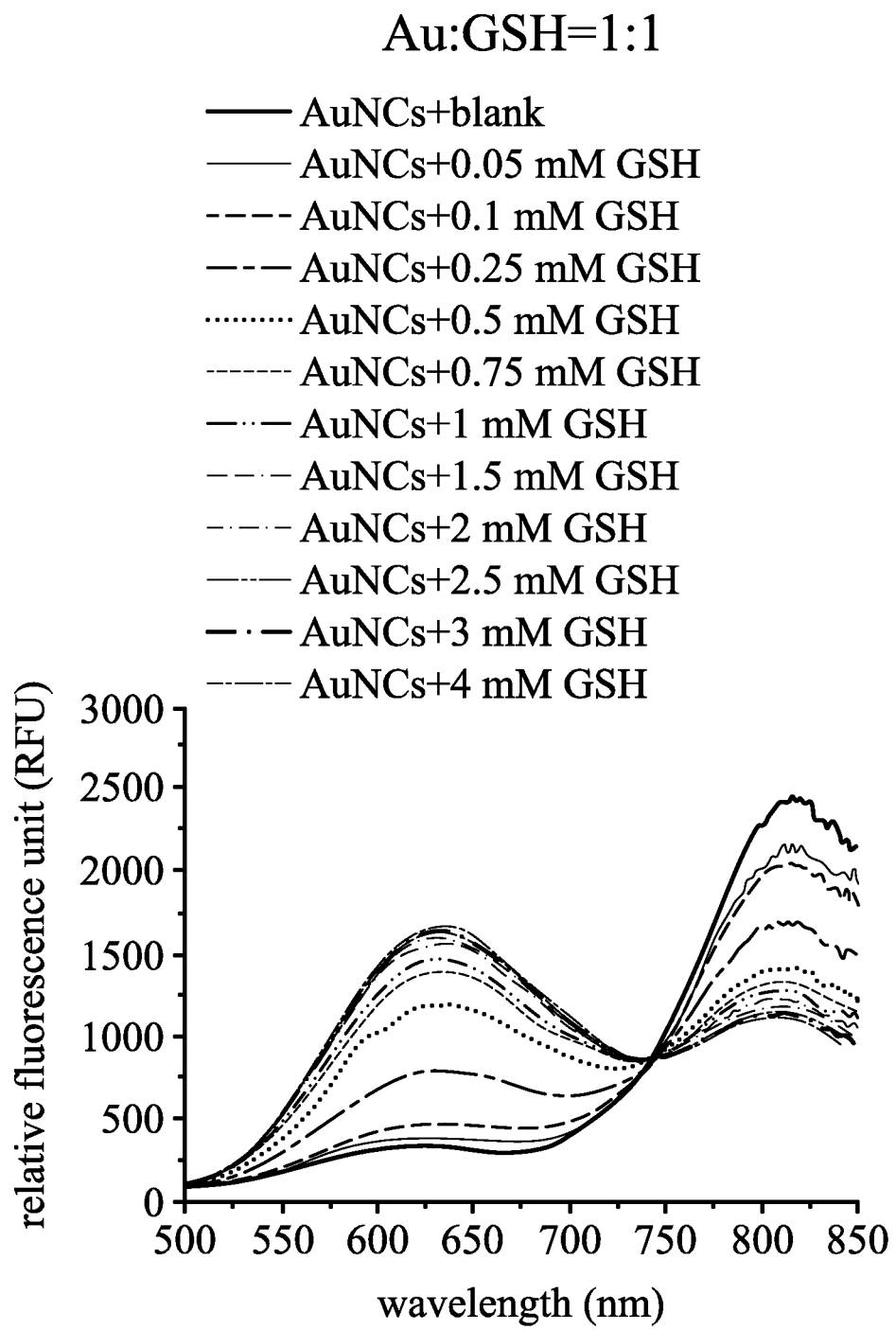
Figure 8B:
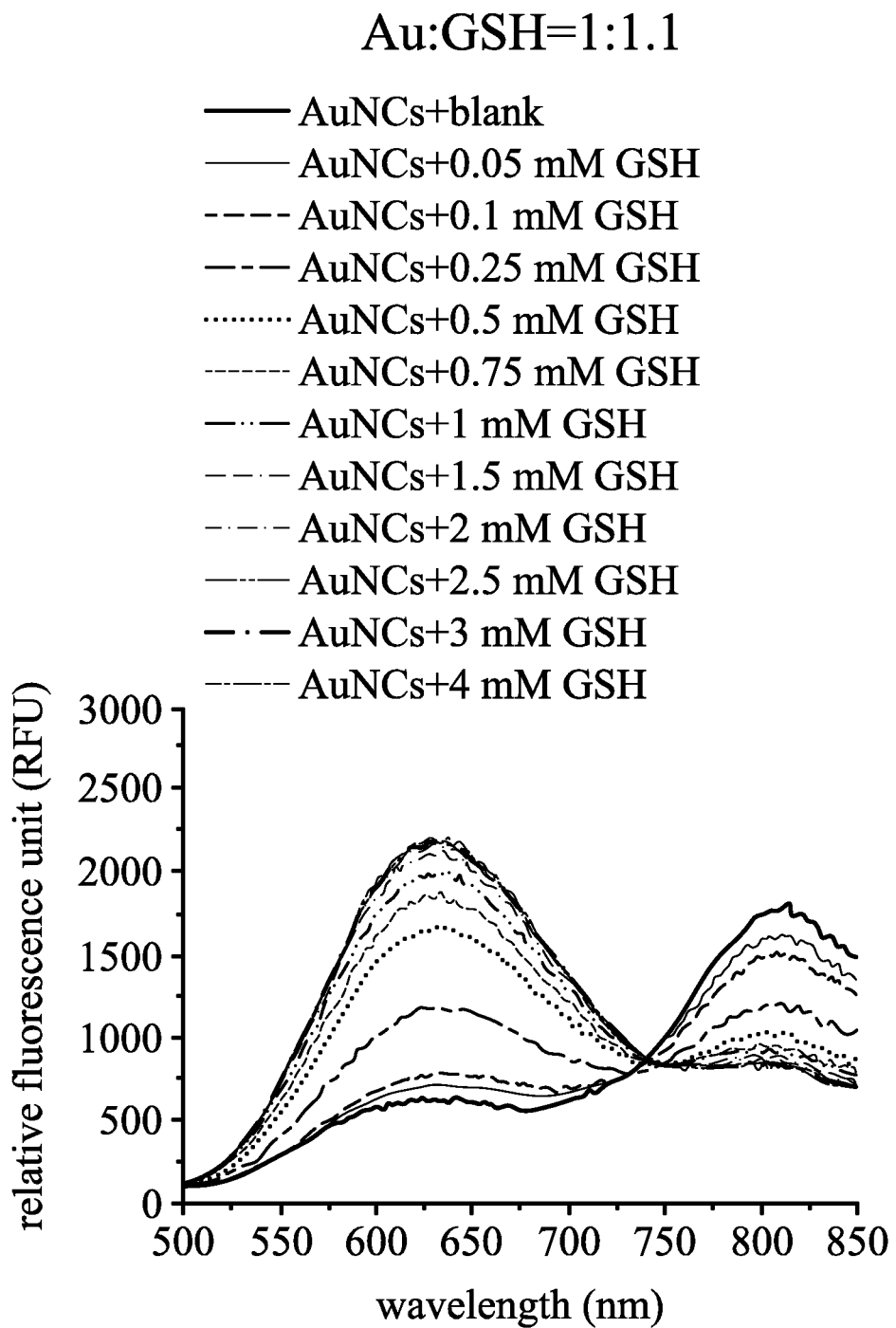
Figure 8C:
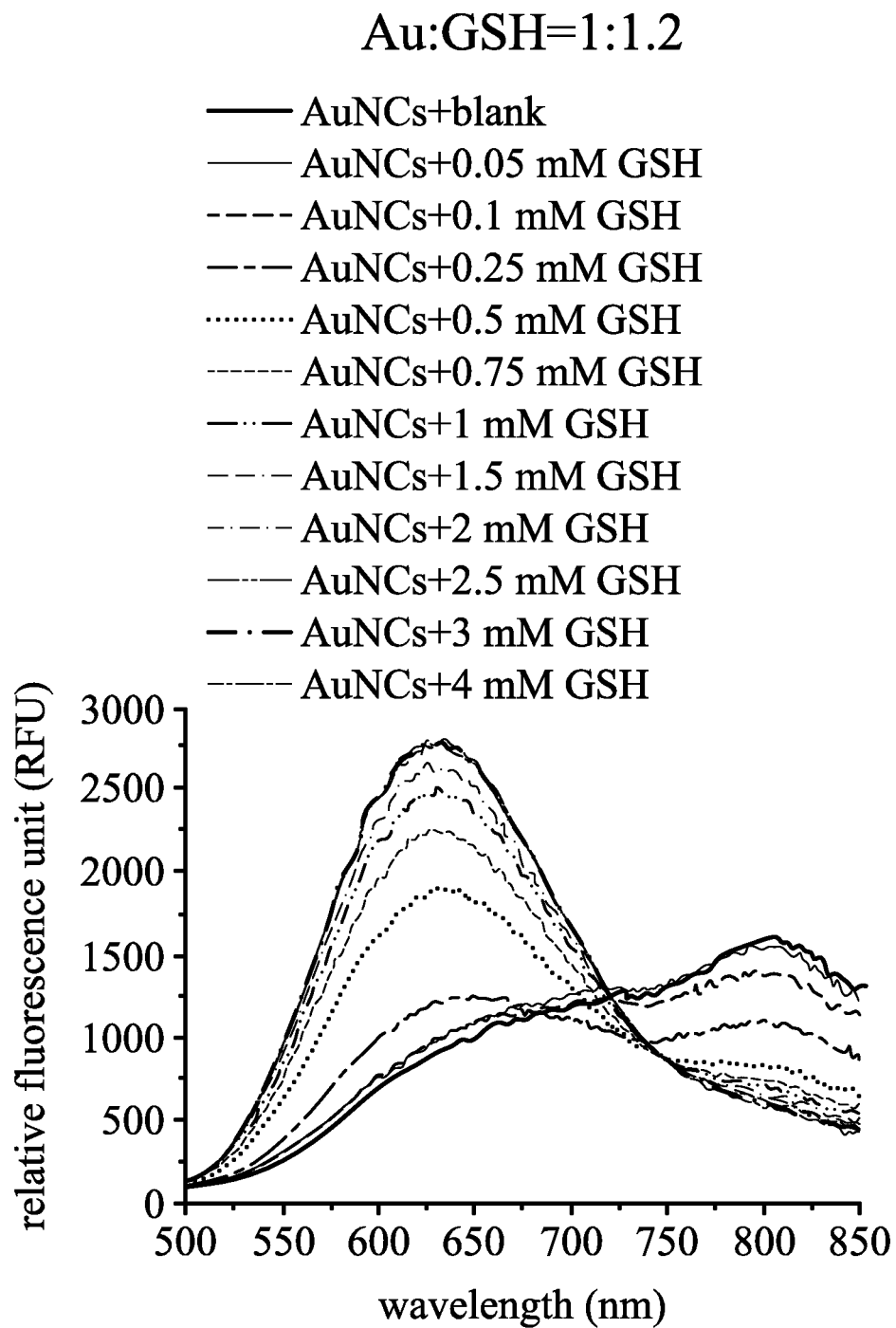
Figure 8D:
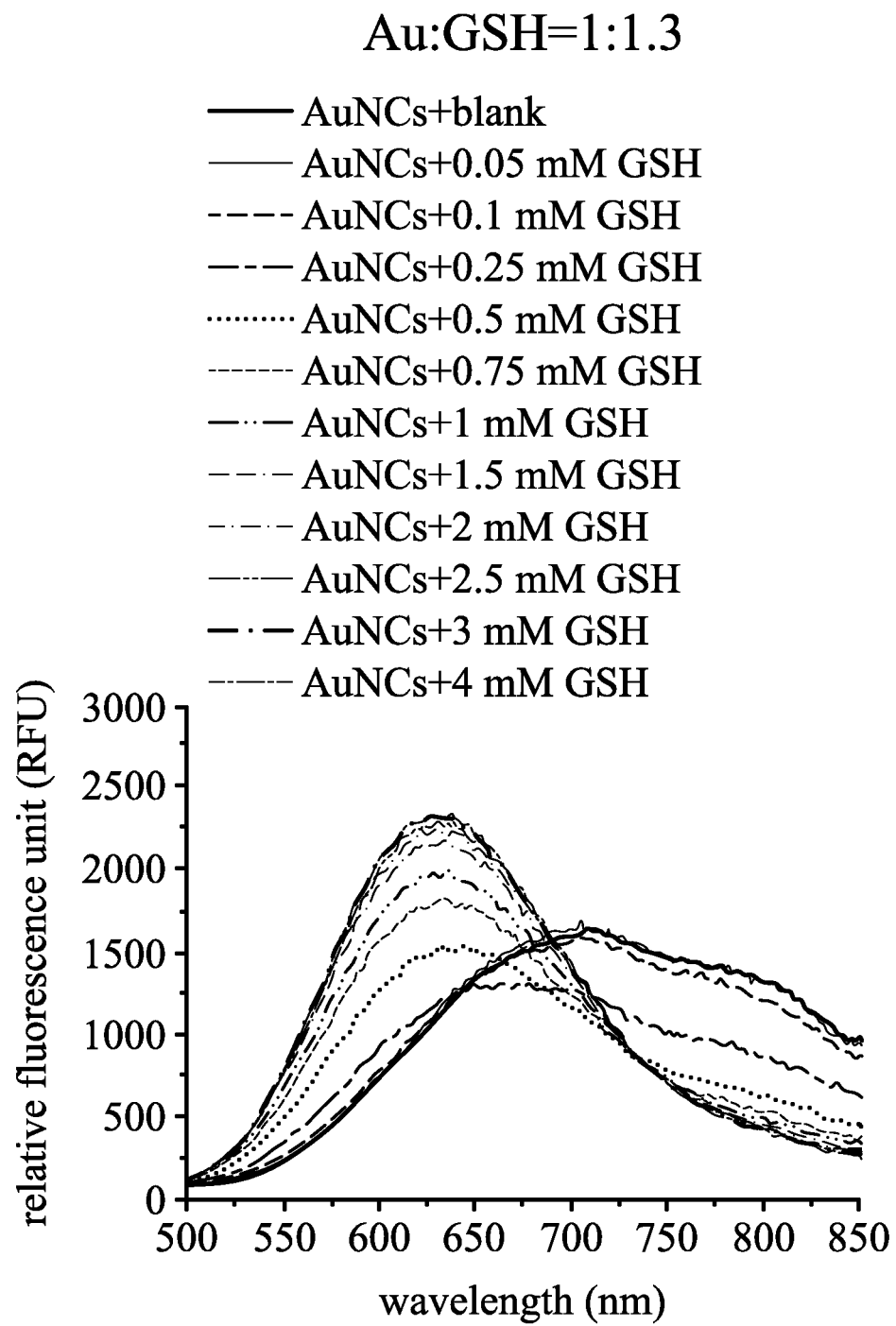
Figure 8E:
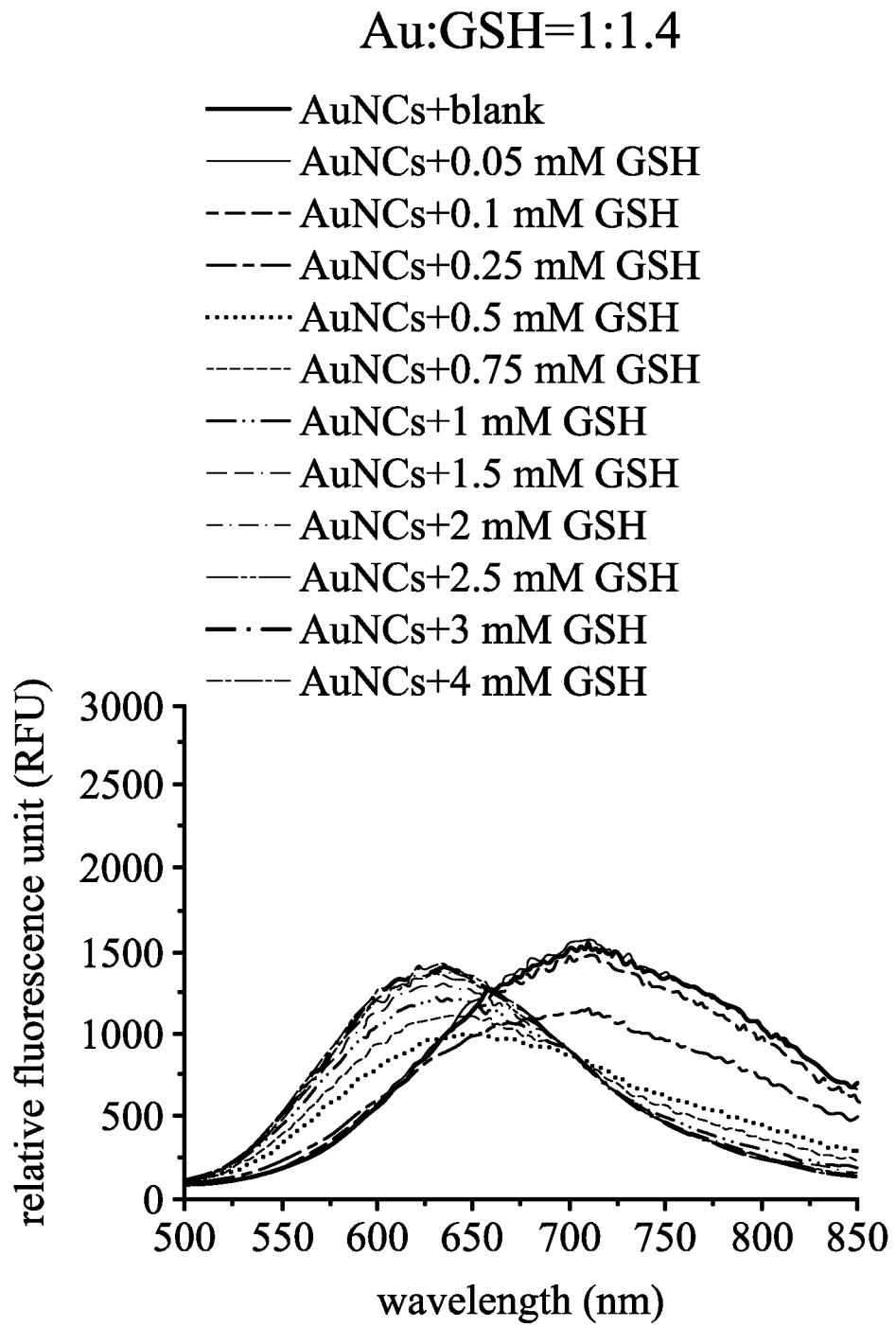
Figure 9A:
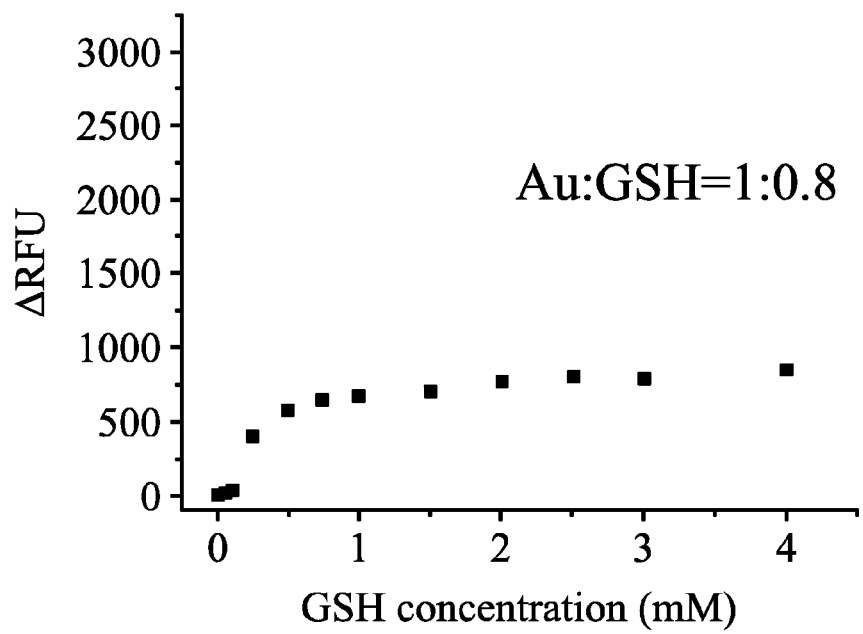
FIGS. 9A-9D, 10A-10D, and 11A-11D show the change of fluorescence intensity of the gold nanocluster compositions (prepared at different molar ratios of gold ions to glutathione) detecting thiol-containing compounds from liquid analytes in embodiments of the disclosure.
Figure 9B:
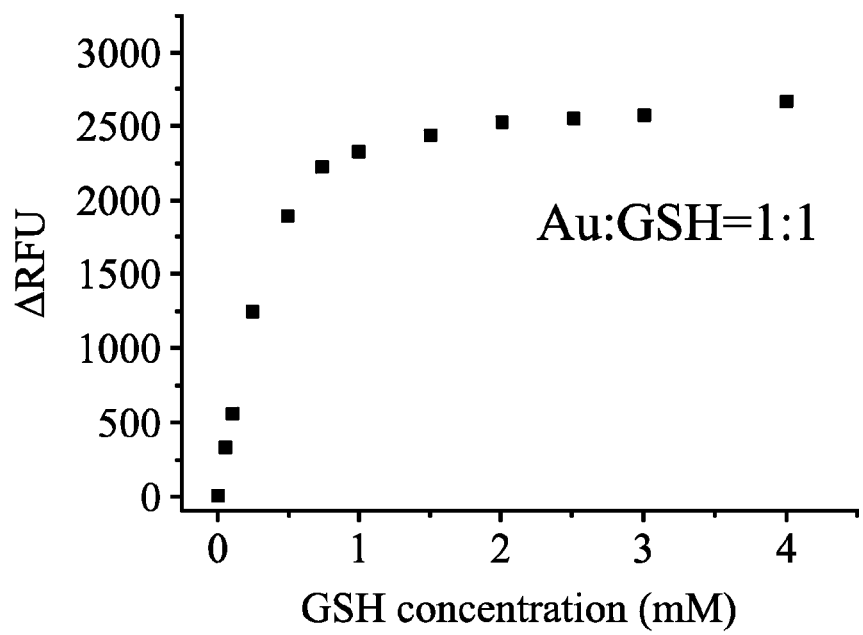
Figure 9C:
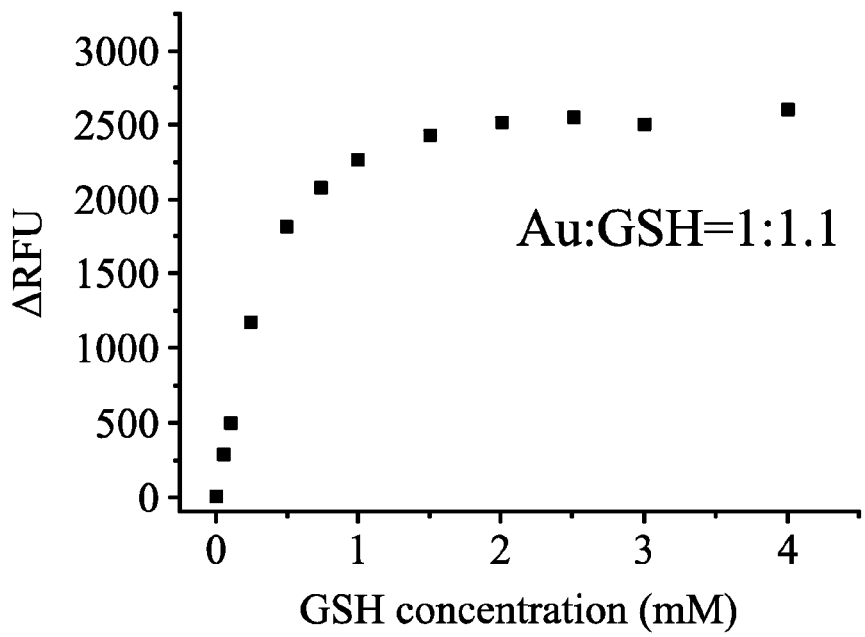
Figure 9D:
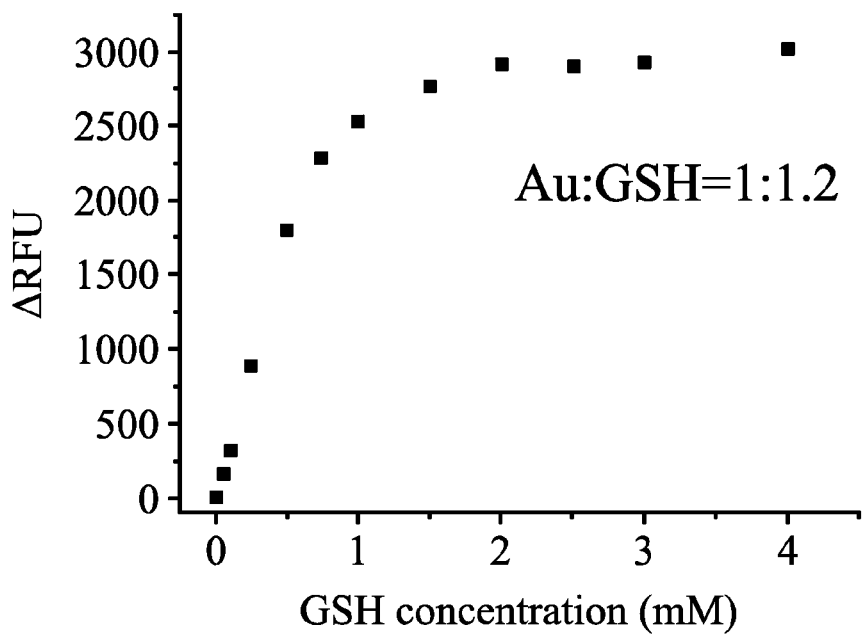
Figure 10A:
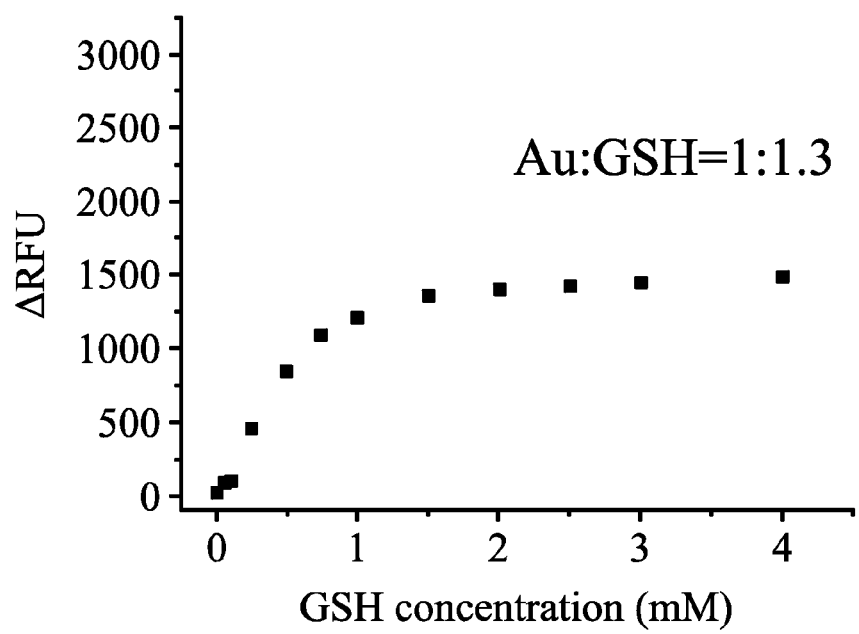
Figure 10B:
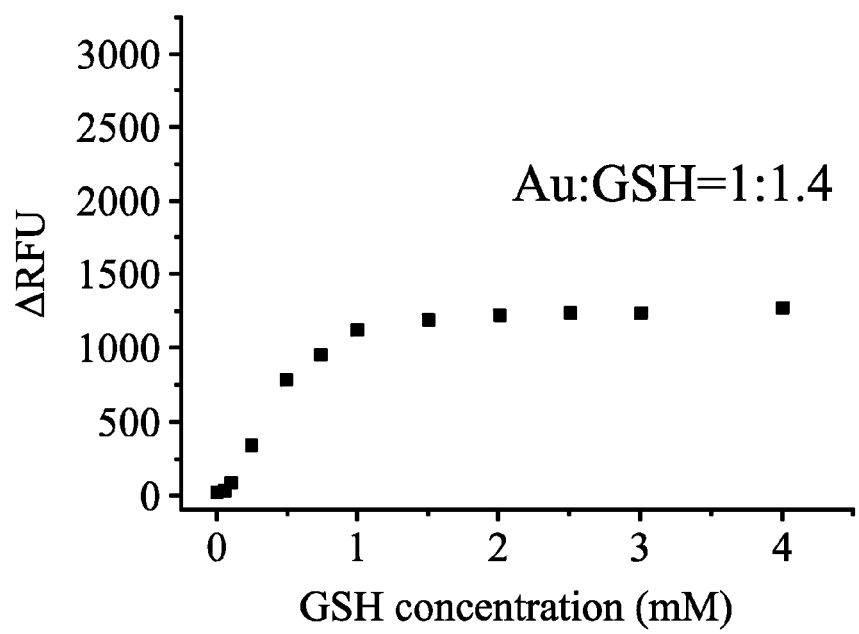
Figure 10C:
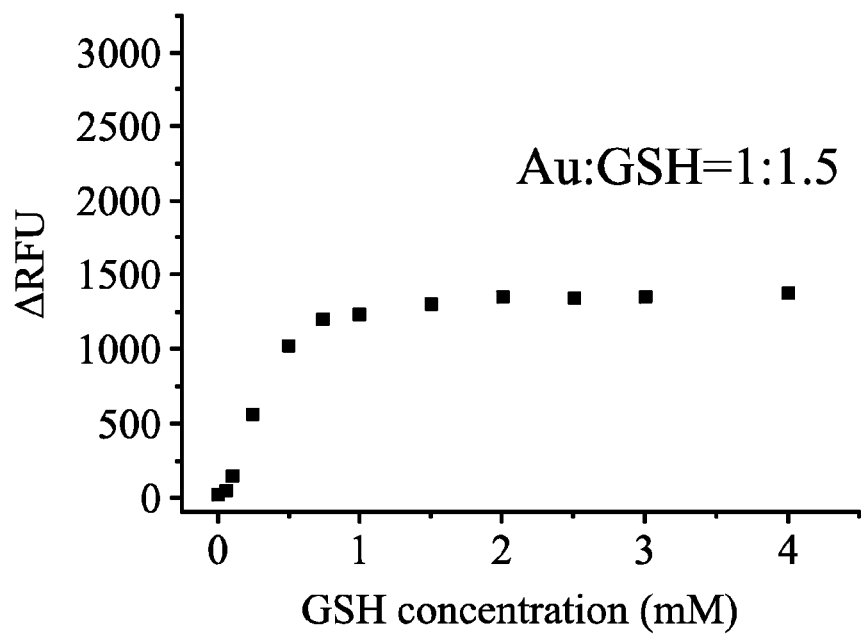
Figure 10D:
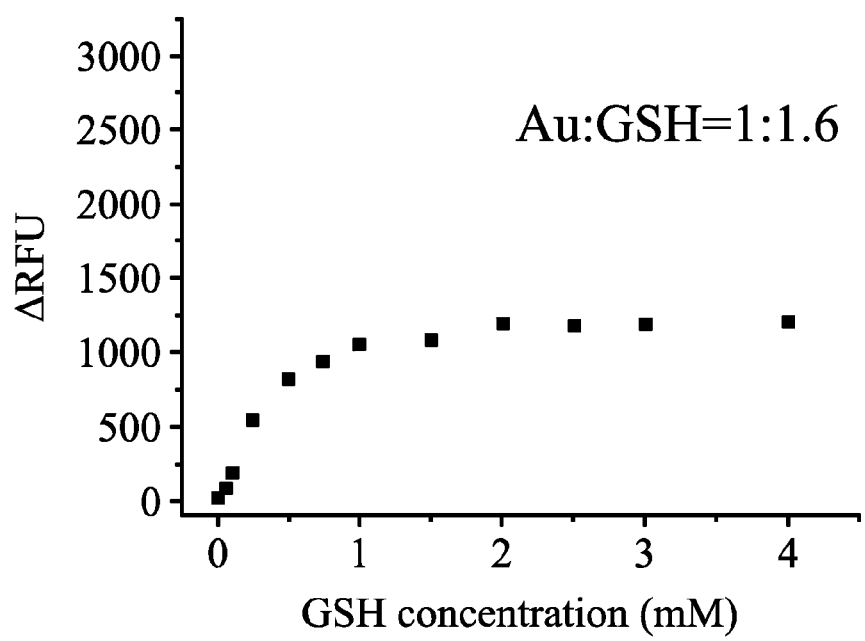

Comparative Example 2 was similar to Example 1, and the difference in Comparative Example 2 was the concentration of GSH solution being changed to achieve different molar ratios of $HAuCl_4$ and GSH, such as Au:GSH=1:1.7, 1:1.8, 1:1.9, and 1:2. The products prepared from the above Au:GSH molar ratios had only one fluorescence emission peak around wavelength of 700 nm. The emission intensities of the products were gradually decreased by increasing the GSH molar ratios, as shown in FIG. 6.

Proof of the Gold Nanoclusters are Partially Capped by GSH

15 µL of GSH solutions of different concentrations (0.05 mM, 0.1 mM, 0.25 mM, 0.5 mM, 0.75 mM, 1 mM, 1.5 mM, 2 mM, 2.5 mM, 3 mM, and 4 mM) were added to 15 µL of the products in Comparative Example 1 (Au:GSH=1:0, 1:0.1, 1:0.2, 1:0.4, and 1:0.6) in the microwell plate, and then evenly mixed for 1 minute. The microwell plate was put into a fluorescence spectroscopy analysis system, and then excited by a light beam with wavelength of 365 nm to analyze the fluorescent properties of the mixtures. As shown in FIGS. 7A-7E, the products in Comparative Example 1 had no obvious fluorescence emission change after adding GSH solutions.

15 µL of GSH solutions of different concentrations (0.05 mM, 0.1 mM, 0.25 mM, 0.5 mM, 0.75 mM, 1 mM, 1.5 mM, 2 mM, 2.5 mM, 3 mM, and 4 mM) were added to 15 µL of the liquid products in Example 1 (Au:GSH=1:1) and Example 3 (Au:GSH=1:1.1, 1:1.2, 1:1.3, and 1:1.4) in the microwell plate, and then evenly mixed for 1 minute. The microwell plate was put into a fluorescence spectroscopy analysis system, and then excited by a light beam with wavelength of 365 nm to analyze the fluorescent properties of the mixtures. As shown in FIGS. 8A-8E, the gold nanocluster compositions in Examples 1 and 3 had enhanced fluorescence intensities at wavelength of 600-650 nm and weakened fluorescence intensities at wavelength of 800-850 nm after adding GSH solutions. Especially when the Au:GSH molar ratios were 1:1, 1:1.1, and 1:1.2 for preparing the gold nanocluster compositions, the intensities of fluorescence emission peak significantly changed. Since the fluorescence of gold nanoclusters originates from the charge transfer between the ligands and gold nanocluster core through the Au—S bonds, as inferred from the above result, the gold nanoclusters were partially capped by GSH. Therefore, the gold nanocluster compositions still had unoccupied sites for further bonding to additional GSH, thereby changing the fluorescence emission intensities thereof.

When the Au:GSH molar ratios were 1:1.3 to 1:1.4, the products had deformed and shifted fluorescence emission spectra with minor intensity changes after adding 15 µL of GSH solutions of different concentrations (0.05 mM, 0.1 mM, 0.25 mM, 0.5 mM, 0.75 mM, 1 mM, 1.5 mM, 2 mM, 2.5 mM, 3 mM, and 4 mM). As inferred from the above result, using higher GSH molar ratio for preparing the gold nanocluster compositions resulted in more GSH bonded on the surface of the gold nanoclusters. Therefore, fewer unoccupied sites on the surface of the gold nanoclusters could be bonded to the further added GSH.

Analysis of the Fluorescence Emission Peak Intensity of the Gold Nanocluster Compositions After Adding Further GSH The sum of the increase of the fluorescence emission intensity at wavelength of 630 nm and the decrease of the fluorescence emission intensity at wavelength of 810 nm was defined as ΔRFU for revealing the relation between the change of fluorescence emission intensity and the concentration of GSH. While the Au:GSH molar ratios were 1:0.8 to 1:1.2, the ΔRFUs as a function of the concentration of the additional added GSH are shown in FIGS. 9A-9D. Because GSH simultaneously served as the reducing agent and the capping agent, as inferred from the above result, lower GSH concentration used during the synthesis tend to form larger gold nanocluster compositions with lower amounts of Au (I) on the surface for bonding to thiols. Thereby causing fewer change of the fluorescence emission intensity after adding additional GSH. The higher GSH concentration used during the synthesis should form smaller gold nanocluster compositions with higher amounts of Au (I) on the surface for bonding to thiols. As such, the fluorescence emission intensity changed significantly after adding additional thiols.

In another example, the Au:GSH molar ratios were 1:1.3 to 1:1.6, such that the surface of the gold nanoclusters was capped by more GSH. As such, their fluorescence emission peak intensity changes were less and saturated earlier after adding additional GSH, as shown in FIGS. 10A-10D.

Figure 11A:
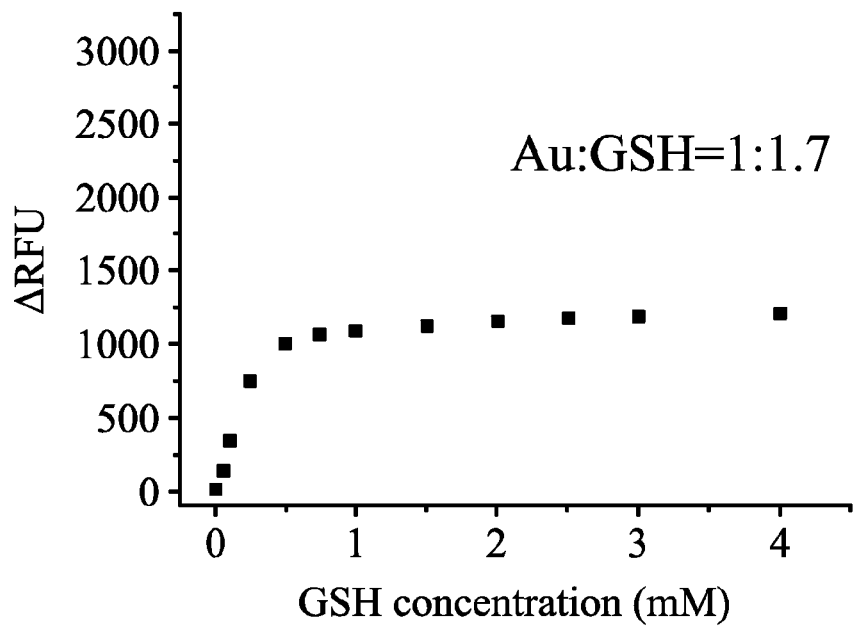
Figure 11B:
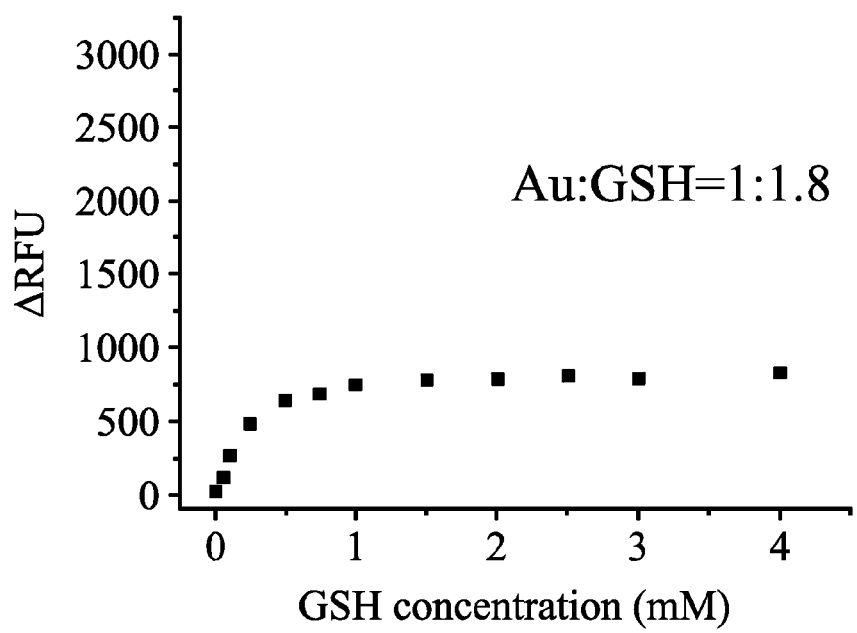
Figure 11C:
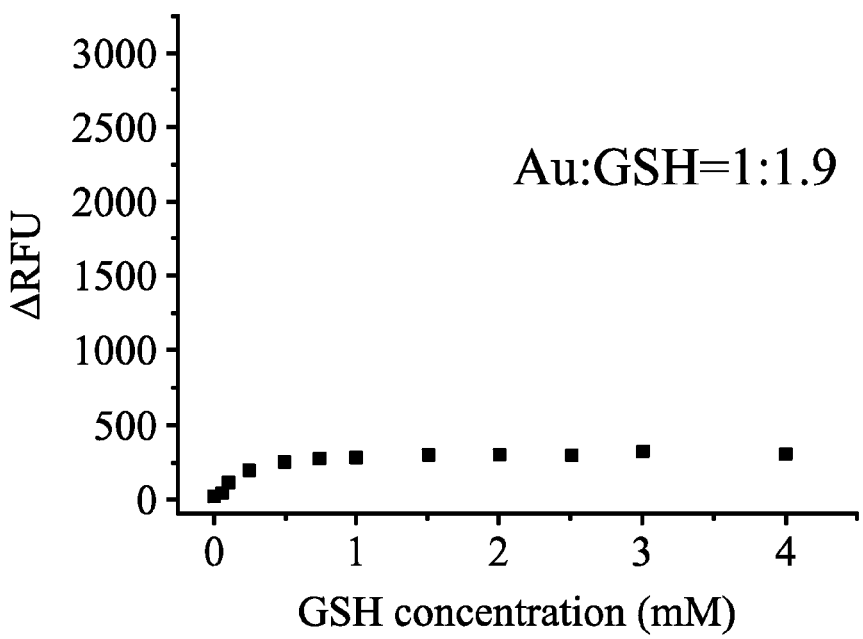
Figure 11D:
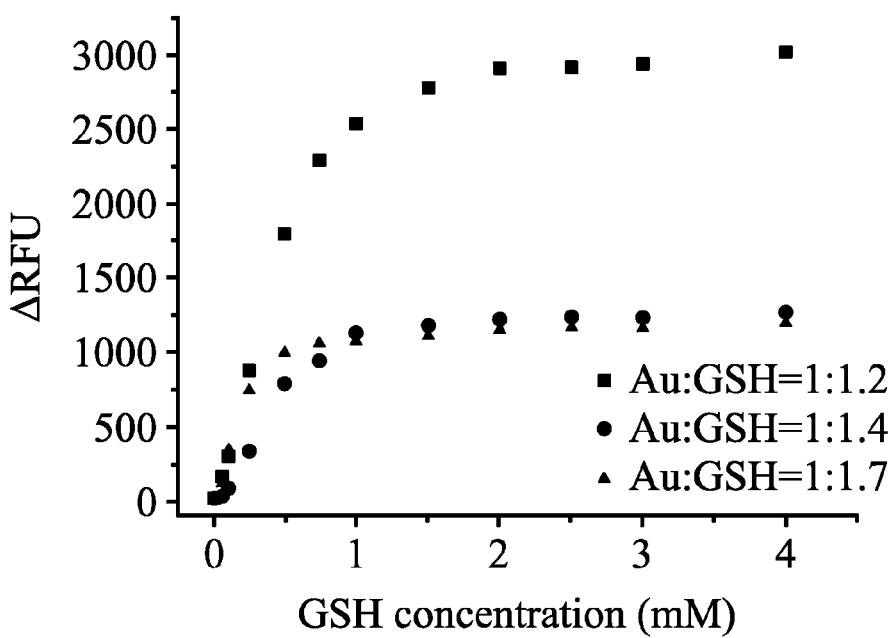
Figure 12:
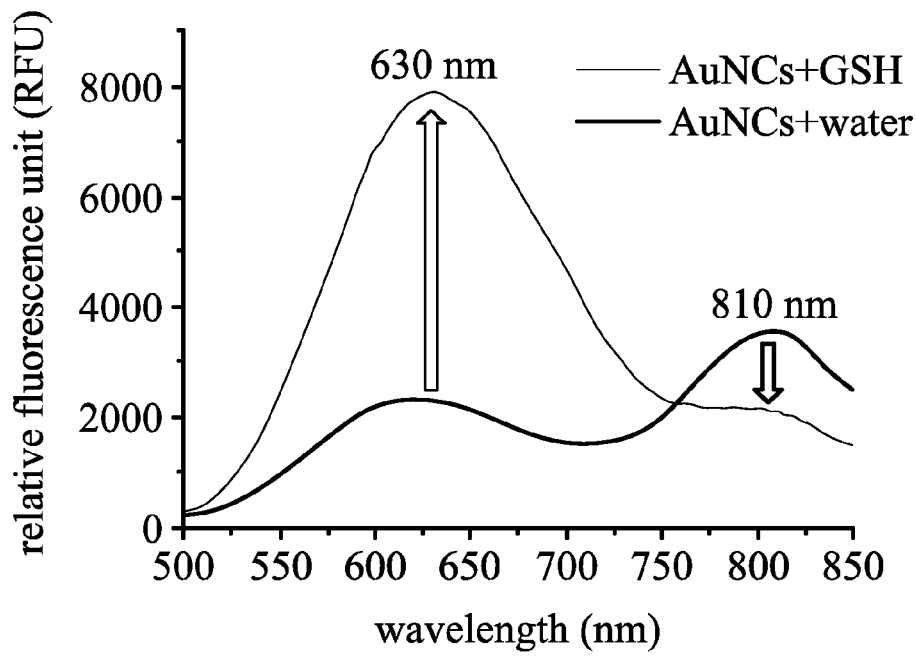
FIG. 12 shows the fluorescence spectrum obtained from the mixture solution of the gold nanocluster compositions and water (or glutathione aqueous solution) in one embodiment of the disclosure.

In a further example, the Au:GSH molar ratios were 1:1.7 to 1:1.9, such that the surface of the gold nanoclusters was capped by more GSH. As such, their fluorescence emission peak intensity changes were less and saturated earlier after adding additional GSH, as shown in FIGS. 11A-11C. FIG. 11D shows a comparison of the Au:GSH molar ratios of 1:1.2, 1:1.4, and 1:1.7.

Referring to the synthesis of the disclosure with Au:GSH molar ratios of 1:0.8 to 1:1.2, the gold nanocluster compositions prepared by more GSH could have enhanced fluorescence emission peaks at wavelength of 600-650 nm and weakened fluorescence emission peaks at wavelength of 800-850 nm, the similar behavior as adding additional GSH. When the gold nanocluster compositions were prepared from a higher GSH concentration, their fluorescence emission peak intensity changes were less and saturated earlier.

As a result, the Au:GSH molar ratio can be controlled to tune the amount of GSH capped on the surface of the gold nanoclusters.

Furthermore, the fluorescence emission spectra of the gold nanocluster compositions changed after reacting with additional added GSH. For example, the fluorescence intensity at wavelength of 630 nm was enhanced, and the fluorescence intensity at wavelength of 810 nm was weakened. Accordingly, the gold nanocluster compositions might serve as sensors for thiol analytes.

Although the above fluorescence emission peak changes could be determined by fluorescence spectra, the fluorescence emission intensity changes could also be determined by naked eye.

Detection of an Aqueous Solution of Thiol-Containing Analytes

First, 0.2 mM of aqueous solution of different analytes were prepared in microcentrifuge tubes. Sample 1 was water, Sample 2 was a glycine solution, Sample 3 was a glutamic acid solution, Sample 4 was a histidine solution, Sample 5 was a methionine solution, Sample 6 was a cystine solution, Sample 7 was an oxidized glutathione solution, Sample 8 was a cysteine solution, Sample 9 was an N-acetylcysteine solution, Sample 10 was a penicillamine solution, Sample 11 was an L-glutathione solution, Sample 12 was a mercaptoethanol solution, and Sample 13 was a cysteine-histidine solution. The aqueous solution of the gold nanocluster compositions in Example 3 (Au:GSH=1:1.1) was selected to detect the thiol-containing compounds, and diluted 10 times with de-ionized water for further use.

15 μL of diluted aqueous solution of the gold nanocluster compositions and 15 μL of a solution of Samples were added to a microcentrifuge tube, respectively, and the tube was then shaken using a vortex mixer for 15 minutes to form mixture solutions. The mixture solutions were added to microwell plates, respectively, which were put into a fluorescence spectroscopy analysis system, and then excited by a light beam with wavelength of 365 nm to analyze the fluorescent property of the mixtures. For example, the fluorescence emission intensity at wavelength of 615 nm (Fx) and the fluorescence emission intensity at wavelength of 815 nm (Fy) of the analytes were recorded. The fluorescence emission intensity at wavelength of 615 nm (F1x) and the fluorescence emission intensity at wavelength of 815 nm (F1y) of Sample 1 were set as blank, and the fluorescence emission intensity changes of the samples were defined as ΔRFU=(Fx−F1x)+F(F1y−Fy). The ΔRFU of Samples were shown in FIG. 13.

Figure 13:
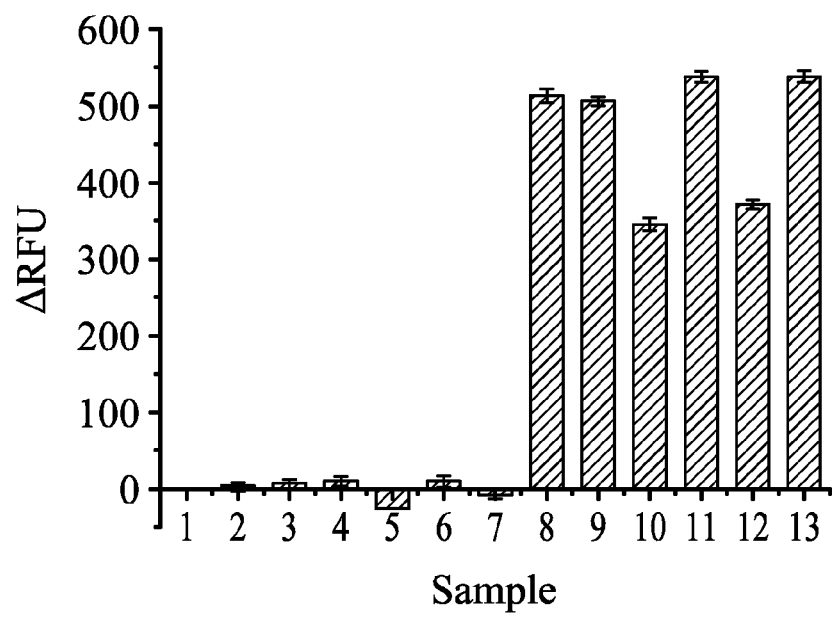
FIG. 13 shows the change of fluorescence intensity obtained from the mixture solution of the gold nanocluster compositions and liquid analytes with or without thiol-containing compounds in one embodiment of the disclosure.

As shown in FIG. 13, the fluorescence emission intensity of the gold nanocluster compositions would change after mixing with a thiol-containing compound, such as Sample 8 (cysteine), Sample 9 (N-acetylcysteine), Sample 10 (penicillamine), Sample 11 (L-glutathione), Sample 12 (mercaptoethanol), and Sample 13 (cysteine-histidine). On the other hand, the fluorescence emission intensity of the gold nanocluster compositions is nearly unaffected after mixing with a compound free of thiol, such as Sample 2 (glycine), Sample 3 (glutamic acid), Sample 4 (histidine), Sample 5 (methionine), Sample 6 (cystine), and Sample 7 (oxidized glutathione). Accordingly, the gold nanocluster compositions of the disclosure were specific to the thiol-containing compounds.

Detection of a Thiol-Containing Gas

The aqueous solution of the gold nanocluster compositions in Example 3 (Au:GSH=1:1.1) was selected to detect the thiol-containing gas, and diluted half with de-ionized water for further use. 0.3 mL of the diluted aqueous solution of the gold nanocluster compositions were added to a microcentrifuge tube. The microcentrifuge tube was opened and fixed in a commercially available airtight container (with a volume of 1.4 L). 1.4 μL of ethanol was dropped into the airtight container and then quickly sealed and put in an oven at 40° C., thereby vaporizing the ethanol to form a vapor with a concentration of 1 ppm. After 30 minutes, the microcentrifuge tube was taken out from the airtight container and the aqueous solution of the gold nanocluster compositions was added to a microwell plate. The microwell plate was put into a fluorescence spectroscopy analysis system, and then excited by a light beam with wavelength of 365 nm to analyze the fluorescent property of the aqueous solution. The above steps were repeated again, and the difference thereof was the ethanol being replaced with mercaptoethanol.

Figure 14:
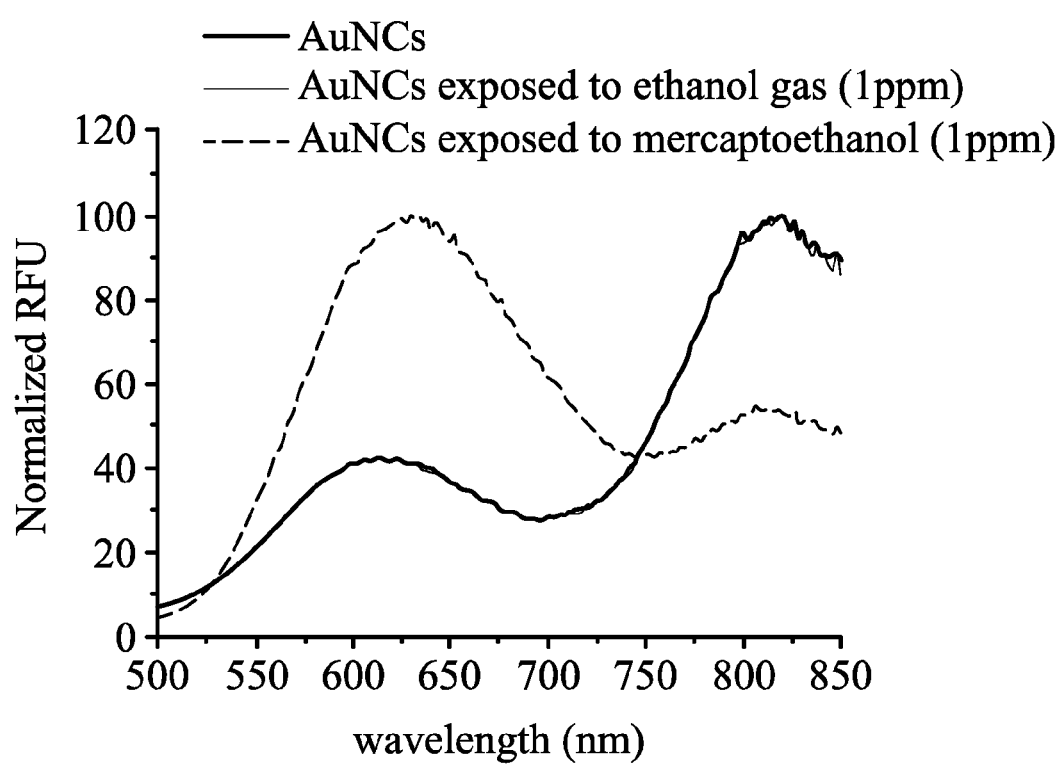
FIG. 14 shows the fluorescence spectra obtained from the mixture solution of the gold nanocluster compositions and gaseous analytes with or without thiol-containing compounds in one embodiment of the disclosure.

As shown in FIG. 14, the aqueous solution contacting the mercaptoethanol vapor had an enhanced fluorescence emission intensity at wavelength of 600-650 nm and a weakened fluorescence emission intensity at wavelength of 800-850 nm. The aqueous solution contacting the ethanol vapor had no fluorescence emission intensity change at wavelength of 600-650 nm and 800-850 nm. Accordingly, the gold nanocluster compositions were specific to the mercaptoethanol vapor.

As shown in above experiments, the gold nanocluster compositions in the disclosure were partially capped by reducing agent. The gold nanocluster compositions could be obtained by controlling the molar ratio of the gold ions and the reducing agent, such that the gold nanocluster compositions had dual fluorescence emission peaks at wavelength of 600-650 nm and 800-850 nm. A liquid (or a gas) with or without a thiol compound could be immediately checked by measuring the change of the fluorescence emission spectra of the gold nanocluster compositions before and after contacting the liquid (or the gas).

It will be apparent to those skilled in the art that various modifications and variations can be made to the disclosed methods and materials. It is intended that the specification and examples be considered as exemplary only, with a true scope of the disclosure being indicated by the following claims and their equivalents.

What is claimed is:
1. A method for preparing a gold nanocluster composition, comprising:
  mixing a gold ion-containing solution and a reducing agent solution to obtain a first mixture liquid; and
  heating the first mixture liquid to obtain a second mixture liquid,
  wherein the second mixture liquid contains a gold nanocluster composition, and the gold nanoclusters are partially capped by reducing agent, and wherein
  when the step of heating the first mixture liquid is performed by microwave heating with a microwave power of 270 W to 450 W and the gold ions and the reducing agent have a molar ratio of 1:1 to 1:1.2, the gold nanocluster compositions have fluorescence emission peaks at wavelength of 600-650 nm and 800-850 nm,
  when the step of heating the first mixture liquid is performed by dry bath heating with a temperature of 100° C. to 200° C. and the gold ions and the reducing agent have a molar ratio of 1:1.1 to 1:1.4, the gold nanocluster compositions have fluorescence emission peaks at wavelength of 600-650 nm and 800-850 nm, and when the step of heating the first mixture liquid is performed by microwave heating with a microwave power of 270 W to 450 W and the gold ions and the reducing agent have a molar ratio of 1:0.7 to 1:0.8, the gold nanocluster composition has a single fluorescence emission peak at wavelength of 800-900 nm.

2. The method as claimed in claim 1, wherein the reducing agent comprises glutathione.

3. The method as claimed in claim 1, wherein the gold ion-containing solution comprises chloroauric acid solution, auric chloride solution, gold sulfide solution, or a combination thereof.

4. The method as claimed in claim 1, wherein the step of heating the first mixture liquid is performed for a period of 10 minutes to 60 minutes.

5. The method as claimed in claim 1, further comprising a step of centrifuging the second mixture liquid and collect the supernatant for obtaining the gold nanocluster compositions.

* * * * *